(12) United States Patent
Makino et al.

(10) Patent No.: US 9,835,612 B2
(45) Date of Patent: Dec. 5, 2017

(54) AUTOMATIC ANALYZER

(71) Applicant: HITACHI HIGH-TECHNOLOGIES CORPORATION, Tokyo (JP)

(72) Inventors: Akihisa Makino, Tokyo (JP); Keiko Yoshikawa, Tokyo (JP); Takeshi Yokokawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 45 days.

(21) Appl. No.: 14/651,684

(22) PCT Filed: Dec. 13, 2013

(86) PCT No.: PCT/JP2013/083407
§ 371 (c)(1),
(2) Date: Jun. 12, 2015

(87) PCT Pub. No.: WO2014/103744
PCT Pub. Date: Jul. 3, 2014

(65) Prior Publication Data
US 2015/0316532 A1 Nov. 5, 2015

(30) Foreign Application Priority Data
Dec. 26, 2012 (JP) .................................. 2012-281936

(51) Int. Cl.
*G01N 33/49* (2006.01)
*G01N 35/02* (2006.01)
(Continued)

(52) U.S. Cl.
CPC ......... *G01N 33/4905* (2013.01); *G01N 33/86* (2013.01); *G01N 35/00663* (2013.01);
(Continued)

(58) Field of Classification Search
None
See application file for complete search history.

(56) References Cited

U.S. PATENT DOCUMENTS

2002/0085959 A1\* 7/2002 Carey .................... B01L 3/508
422/400
2004/0023404 A1 2/2004 Shibata
(Continued)

FOREIGN PATENT DOCUMENTS

| JP | 06-040837 U | 5/1994 |
| JP | 3037641 U | 3/1997 |

(Continued)

OTHER PUBLICATIONS

International Search Report.
Chinese Office Action received in corresponding Chinese Application No. 201380066008.1 dated Feb. 19, 2016.

*Primary Examiner* — Sean E Conley
*Assistant Examiner* — Benjamin R Whatley
(74) *Attorney, Agent, or Firm* — Mattingly & Malur, PC

(57) ABSTRACT

An automatic analyzer which realizes stable reagent heating and high dispensing accuracy includes a thermostat bath for controlling a reagent or a reaction solution in reaction cells arranged on a circumference of a reaction disk to have a constant temperature; a first reagent dispensing mechanism dispenses a reagent into the reaction cells; a photometer detects transmitted light or scattered light in the reaction cell; and a disposable reaction container for allowing the sample and the reagent to mix and react with each other. The analyzer also includes a second reagent dispensing mechanism with a reagent heating function which dispenses the reagent into the disposable reaction container; a coagulation time detection section; a reaction container temperature control block; a reagent dispensing syringe which is connected to the second reagent dispensing mechanism; and a
(Continued)

fluid temperature control mechanism which controls the temperature of an internal fluid of the reagent dispensing syringe.

15 Claims, 6 Drawing Sheets

(51) Int. Cl.
    *G01N 35/00*     (2006.01)
    *G01N 35/10*     (2006.01)
    *G01N 33/86*     (2006.01)

(52) U.S. Cl.
    CPC ....... *G01N 35/025* (2013.01); *G01N 35/1002* (2013.01); *G01N 35/1016* (2013.01); *G01N 2035/00346* (2013.01); *G01N 2035/00376* (2013.01); *G01N 2035/00386* (2013.01); *G01N 2035/00425* (2013.01); *G01N 2035/00435* (2013.01); *G01N 2035/00673* (2013.01); *G01N 2035/1048* (2013.01)

(56) References Cited

U.S. PATENT DOCUMENTS

| | | | |
|---|---|---|---|
| 2008/0044311 A1* | 2/2008 | Iguchi | G01N 35/1009 422/63 |
| 2008/0063573 A1* | 3/2008 | Ammann | B01L 7/52 422/105 |
| 2008/0105033 A1* | 5/2008 | Tipler | G01N 30/30 73/23.42 |
| 2008/0183431 A1* | 7/2008 | Matsuo | G01N 15/12 702/187 |
| 2008/0213132 A1* | 9/2008 | Watari | G01N 35/1016 422/68.1 |
| 2010/0248346 A1* | 9/2010 | Kaneko | G01N 35/1002 435/287.1 |
| 2011/0223064 A1* | 9/2011 | Katsumi | G01N 35/1002 422/73 |
| 2011/0232769 A1* | 9/2011 | Nichogi | G01N 35/025 137/3 |
| 2012/0048036 A1* | 3/2012 | Mimura | G01N 35/025 73/863.01 |

FOREIGN PATENT DOCUMENTS

| | | | |
|---|---|---|---|
| JP | 2000-321286 A | | 11/2000 |
| JP | 2004-37161 A | | 2/2004 |
| JP | 2007-322327 A | | 12/2007 |
| JP | 2008-70355 A | | 3/2008 |
| JP | 2008-203009 A | | 9/2008 |
| JP | 2010-286243 A | | 12/2010 |
| JP | 2010286243 A | * | 12/2010 |
| JP | 2011-99681 A | | 5/2011 |
| JP | 2012-159392 A | | 8/2012 |

* cited by examiner

[FIG. 1]
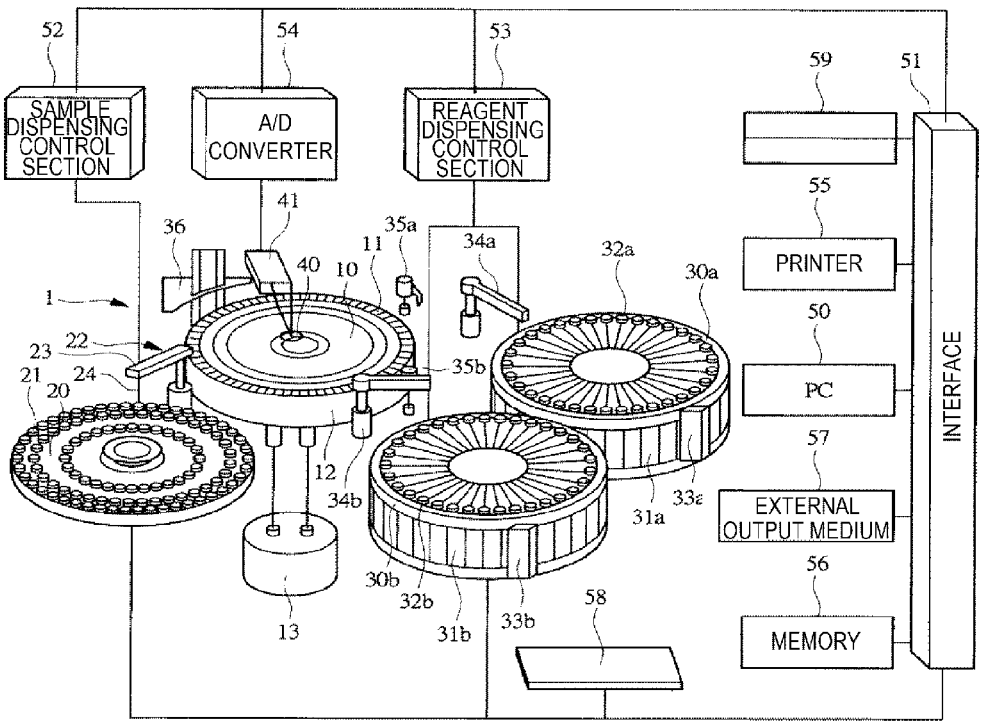
[FIG. 2]
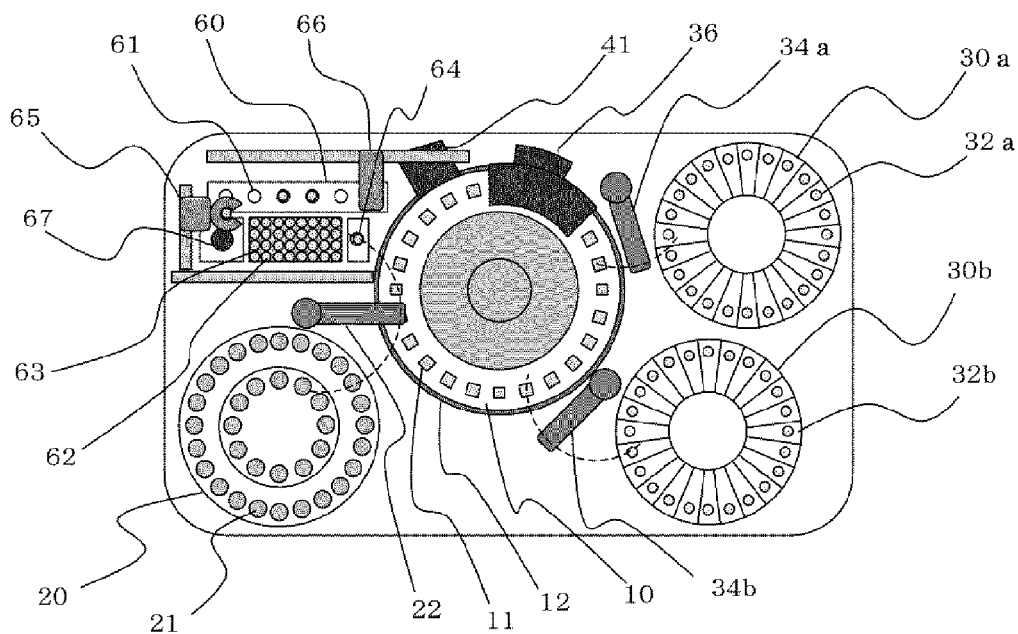

[FIG. 3]
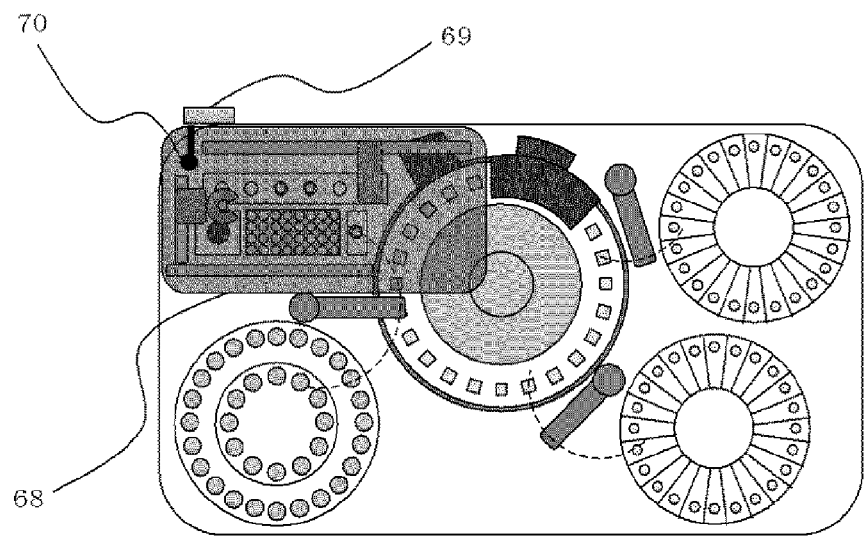
[FIG. 4]
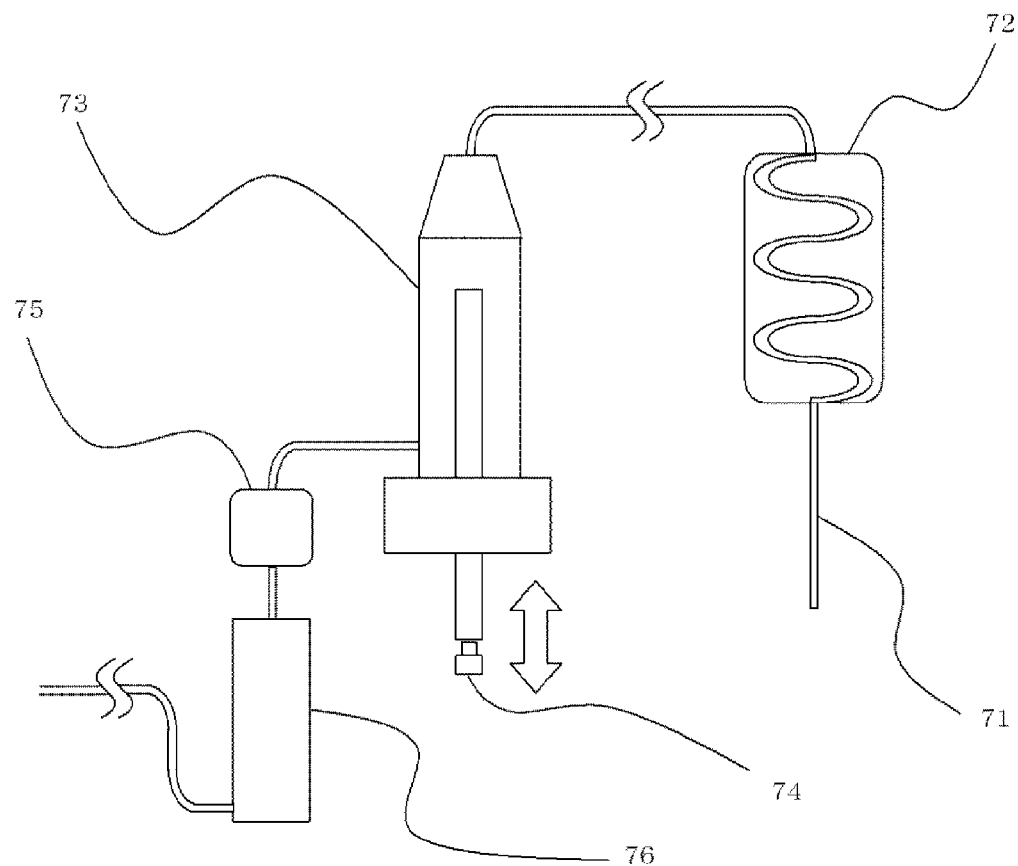

[FIG. 5]
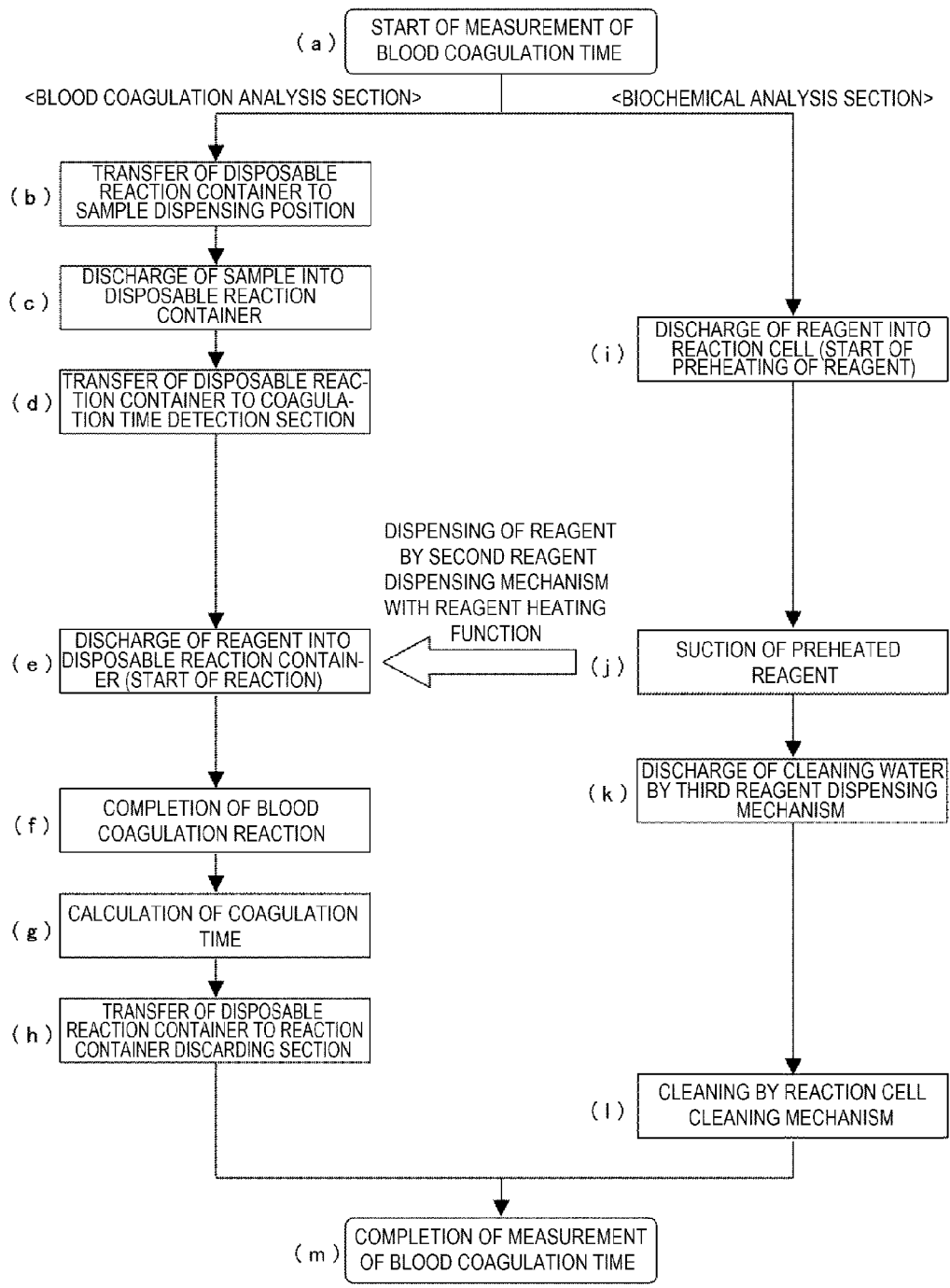

[FIG. 6]
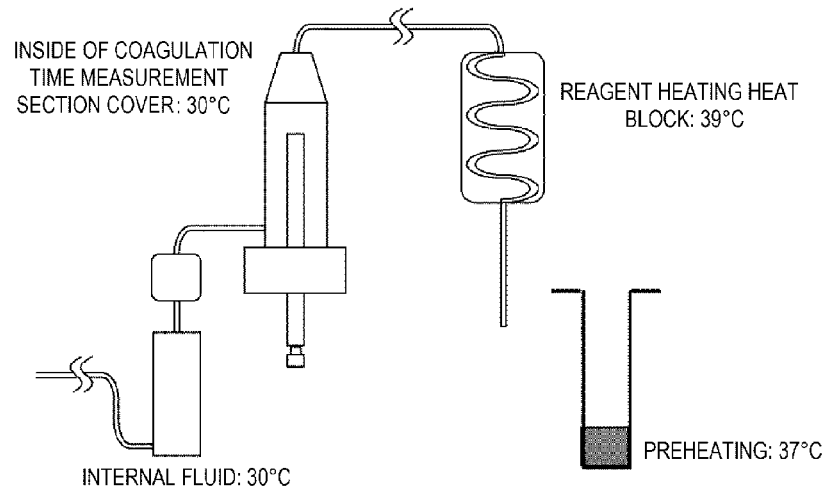
[FIG. 7]
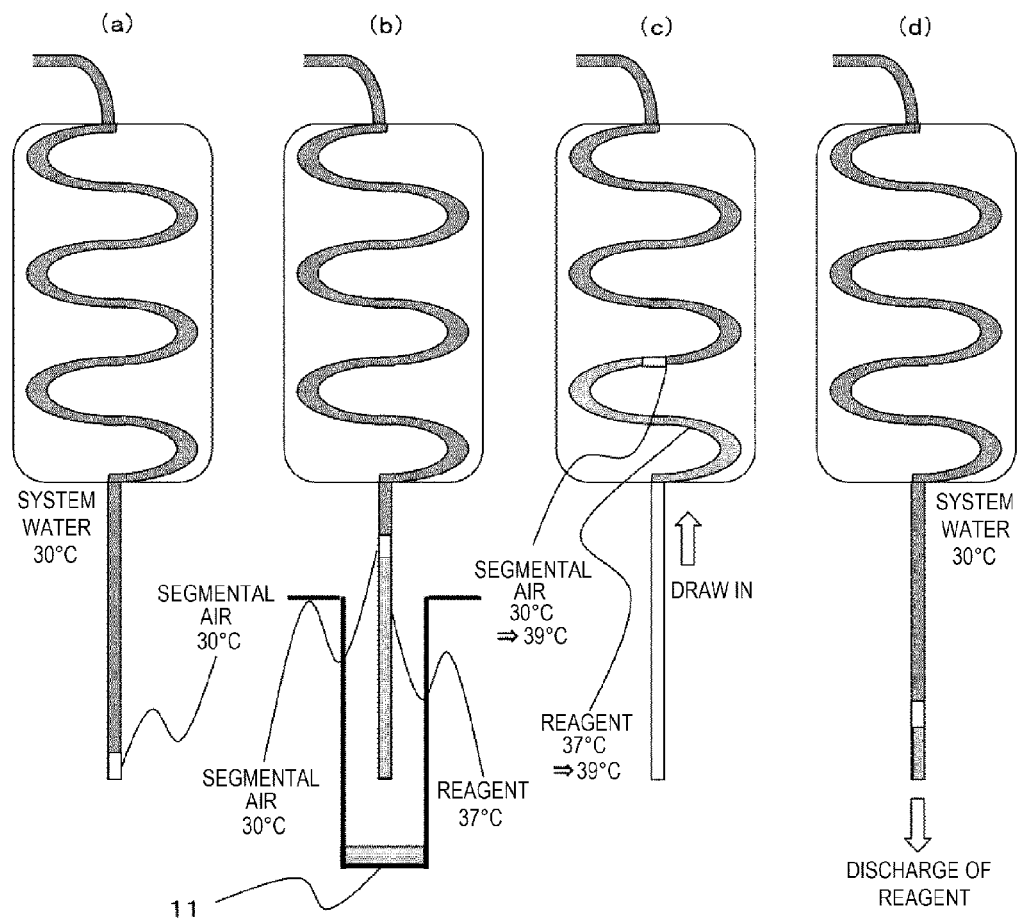

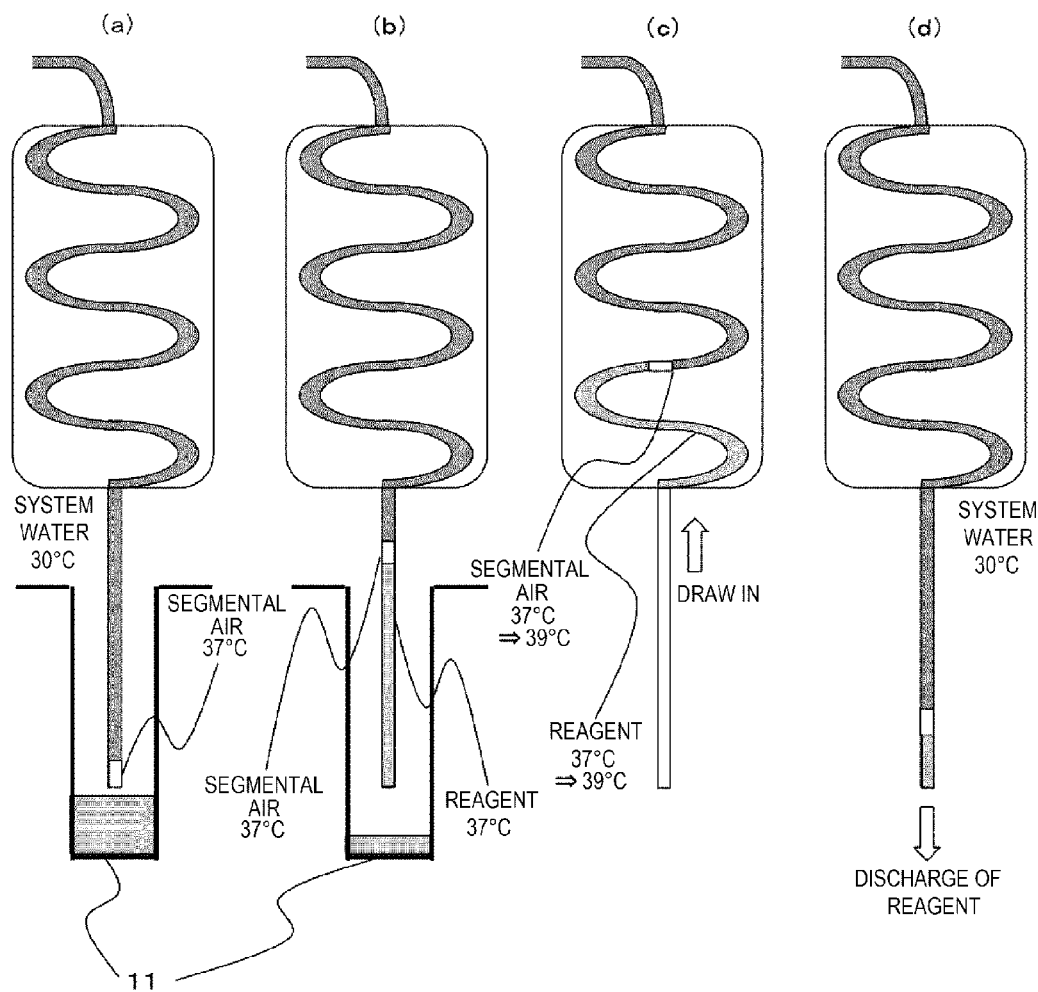
[FIG. 8]

[FIG. 9]
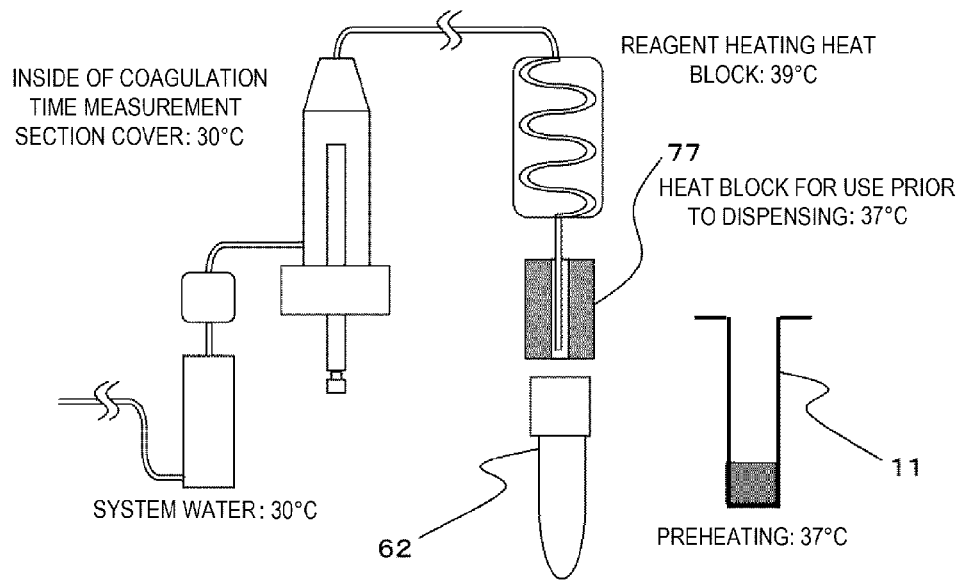
[FIG. 10]
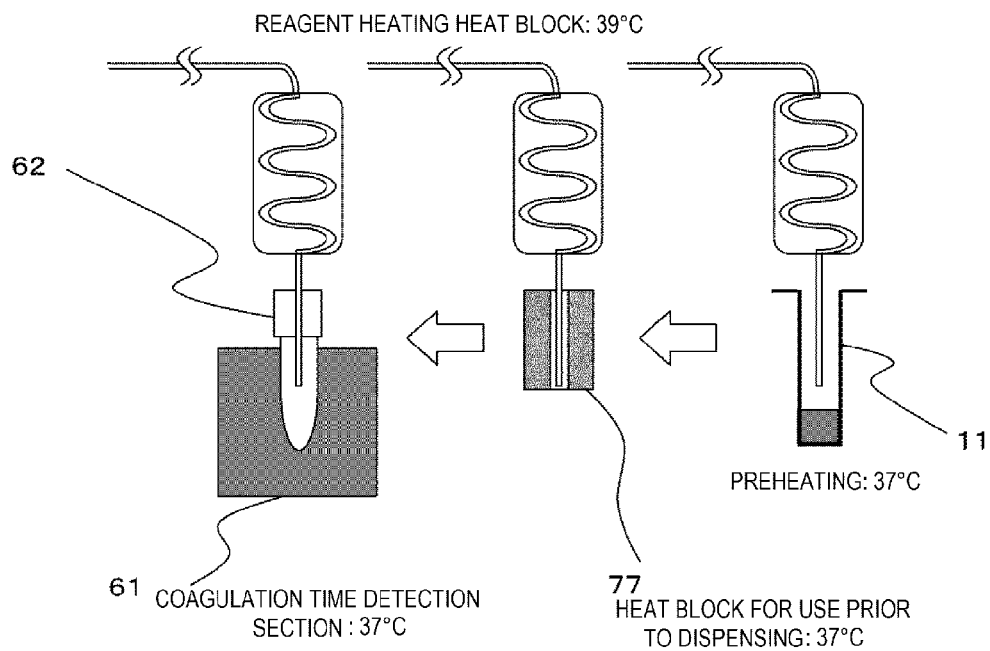

AUTOMATIC ANALYZER

TECHNICAL FIELD

The present invention relates to an automatic analyzer which analyzes the amount of a component contained in a sample such as blood or urine, and particularly relates to an automatic analyzer which can measure items of a blood coagulation time and coagulation-fibrinolysis markers.

BACKGROUND ART

Blood maintains its fluidity in blood vessels and flows therethrough. However, once bleeding occurs, a coagulation factor present in plasma or platelets is activated in a chain reaction, and fibrinogen in plasma is converted into fibrin, and the fibrin is deposited, whereby bleeding is arrested. Such blood coagulation includes an extrinsic one in which blood leaking outside the blood vessel coagulates and an intrinsic one in which blood coagulates in the blood vessel. The measurement items with respect to blood coagulability (coagulation time) include a prothrombin time (PT) in an extrinsic blood coagulation reaction test, an activated partial thromboplastin time (APTT) and a fibrinogen level (Fbg) in an intrinsic blood coagulation reaction test, and the like.

All these items are measured by detecting fibrin deposited by adding a reagent to start coagulation using an optical, physical, or electrical technique. As the method using an optical technique, there is known a method in which light is irradiated onto a reaction solution, and fibrin deposited in the reaction solution is detected as a change in the intensity of scattered light or transmitted light over time, whereby the time when fibrin starts to deposit is calculated. Further, in the field of blood coagulation-fibrinolysis test, other than the measurement of a blood coagulation time, also the measurement of a coagulation factor and the measurement of coagulation-fibrinolysis markers are also included. In the measurement of a coagulation factor, the measurement is performed mainly in a blood coagulation time measurement section, however, coagulation-fibrinolysis markers are analyzed using an absorptiometer by a synthetic substrate method, a latex agglutination method, or the like.

In an automatic blood coagulation analyzer represented by PTL 1, it is necessary to report the result of the measurement of a coagulation time in 0.1 second unit and it is necessary to perform continuous photometry, and since it is impossible to recycle a reaction container by cleaning when a reaction solution is coagulated, the reaction is performed in an independent photometric port, and the reaction container is disposable. Further, the coagulation time is as short as several seconds, and therefore, it is necessary that the temperature should reach 37° C. which is the temperature condition required for the reaction immediately after a sample and a reagent are mixed with each other. The reagent is generally stored in a reagent cool box at 5 to 10° C., and in order to heat the reagent, a reagent dispensing mechanism for a reagent for use in the item of a coagulation time is provided with a reagent heating function.

CITATION LIST

Patent Literature

PTL 1: JP-A-2000-321286
PTL 2: JP-A-2004-37161
PTL 3: JP-A-2008-70355
PTL 4: Japanese Utility Model No. 3,037,641
PTL 5: JP-A-2008-203009

SUMMARY OF INVENTION

Technical Problem

The essential conditions for analyzing the item of a blood coagulation time with good reproducibility are stable reagent heating and dispensing of a reagent with good reproducibility.

With respect to the reagent heating, there was a problem that the control of the temperature of the reagent discharged becomes unstable because of the following reasons: (1) a change in the heating conditions due to a variation in the temperature outside the device; (2) a variation in the temperature of the tip end of a reagent nozzle due to a variation in the temperature outside the device; (3) a temperature fall of a temperature control section when the reagent nozzle is cleaned due to a variation in the temperature of supply water to the device, etc.

With respect to (1), in PTL 2 and PTL 3, a technique for changing the conditions for heating the reagent by monitoring the outside temperature is described. However, even when only the outside temperature is monitored, if the temperature of supply water is unstable, a problem arises that the discharge temperature becomes unstable or it takes time to stabilize the temperature of the heating section.

Further, with respect to (2), in PTL 4, the temperature is controlled with a heater up to the vicinity between the tip ends of the reagent nozzles, however, it is necessary to increase the size of a suction port of a reagent bottle because the tip end of the reagent nozzle is thickened, and therefore, there is a concern that the storage state of the reagent or the like may be affected. Further, in the case where the nozzle is exchanged due to the degradation over time or breakage of the nozzle, or the like, the nozzle is exchanged with an expensive nozzle.

With respect to (3), a technique for improving the dispensing accuracy by controlling the temperature of supply water to the device in the device is introduced by PTL 5, however, the technique is not related to the temperature control performance of the reagent dispensing mechanism with a reagent heating function, and therefore is not a technique for suppressing a dispersion of the variation in the temperature of the reagent heating section.

An object of the invention is to provide an automatic analyzer which can perform an analysis with high reproducibility by realizing stable reagent heating and high dispensing accuracy regardless of a variation in the temperature outside the device and the temperature of supply water to the device.

Solution to Problem

The automatic analyzer of the invention for achieving the above object is an automatic analyzer including: a reaction disk, on which reaction cells for allowing a sample and a reagent to mix and react with each other are arranged on the circumference thereof, and which alternately repeats rotation and stop; a thermostat bath for controlling the reagent or a reaction solution in the reaction cell to have a constant temperature; a first reagent dispensing mechanism which dispenses the reagent into the reaction cell; a photometer which detects transmitted light or scattered light by irradiating light onto the reaction solution in the reaction cell; a reaction container supply section which supplies a disposable reaction container for allowing the sample and the reagent to mix and react with each other; a second reagent dispensing mechanism with a reagent heating function which dispenses the reagent into the disposable reaction container; a coagulation time detection section which detects transmitted light or scattered light by irradiating light onto the reaction solution in the disposable reaction container; a reaction container temperature control block which has the coagulation time detection section and is used for controlling the reagent or the reaction solution in the disposable reaction container to have a constant temperature; a reagent dispensing syringe which is connected to the second reagent dispensing mechanism with a heating function; and a fluid temperature control mechanism which controls the temperature of an internal fluid of the reagent dispensing syringe.

Advantageous Effects of Invention

According to the invention, an automatic analyzer which can perform an analysis with high reproducibility can be provided by realizing stable reagent heating and high dispensing accuracy regardless of a variation in the temperature outside the device and the temperature of supply water to the device.

BRIEF DESCRIPTION OF DRAWINGS

FIG. 1 is a system block diagram showing the overall configuration of an automatic analyzer of a turn table system serving as abase according to an embodiment of the invention.

FIG. 2 is a schematic view of an automatic analyzer provided with a biochemical analysis section of a turn table system and a coagulation time measurement section according to an embodiment of the invention.

FIG. 3 is a view showing a coagulation time measurement section cover according to an embodiment of the invention.

FIG. 4 is a schematic view of a flow channel of a reagent dispensing mechanism with a heating function according to an embodiment of the invention.

FIG. 5 shows one example of a coagulation time measurement sequence according to an embodiment of the invention.

FIG. 6 is a view showing one example of a state of controlling the temperature around the reagent dispensing mechanism with a heating function according to an embodiment of the invention.

FIGS. 7(a) to 7(d) are views showing the flow of a dispensing operation in the case where segmental air is sucked inside the coagulation time measurement section cover according to an embodiment of the invention.

FIGS. 8(a) to 8(d) are views showing the flow of a dispensing operation in the case where segmental air is sucked inside a reaction cell according to an embodiment of the invention.

FIG. 9 is a view showing a reagent dispensing mechanism provided with a block which makes the temperature around a reagent probe constant when discharging a reagent according to an embodiment of the invention.

FIG. 10 is a view showing one example of an operation of the reagent dispensing mechanism provided with a block which makes the temperature around a reagent probe constant when discharging a reagent according to an embodiment of the invention.

DESCRIPTION OF EMBODIMENTS

Hereinafter, embodiments of the invention will be described in detail with reference to the drawings. Note that components having the same function are denoted by the same reference signs throughout the drawings for describing the embodiments in principle, and the repetitive description thereof will be omitted as much as possible.

FIG. 1 is a system block diagram showing the overall configuration of an automatic analyzer of a turn table system serving as a base according to an embodiment of the invention. As shown in FIG. 1, an automatic analyzer 1 is mainly composed of a reaction disk 10, a sample disk 20, a first reagent disk 30a, a second reagent disk 30b, a light source 40, a photometer 41, and a computer 50.

The reaction disk 10 is intermittently rotatably provided, and on the disk, a number of reaction cells 11 made of a light transmitting material are arranged along the circumferential direction. The reaction cells 11 are maintained at a predetermined temperature (for example 37° C.) by a thermostat bath 12. The temperature of a fluid in the thermostat bath 12 is controlled by a thermostat device 13. The thermostat bath 12 can control a reagent or a reaction solution in the reaction cell 11 to have a constant temperature.

On the sample disk 20, a number of specimen containers 21 for storing a biological sample such as blood or urine are placed doubly along the circumferential direction in an example shown in the drawing. Further, a sample dispensing mechanism 22 is disposed in the vicinity of the sample disk 20. This sample dispensing mechanism 22 is mainly composed of a movable arm 23 and a pipette nozzle 24 attached thereto. According to this configuration, in the sample dispensing mechanism 22, the pipette nozzle 24 is appropriately moved to a dispensing position by the movable arm 23 when dispensing the sample, sucks a predetermined amount of the sample therein from the specimen container 21 positioned at a sucking-in position on the sample disk 20, and discharges the sample into the reaction cell 11 present at a discharge position on the reaction disk 10.

The first reagent disk 30a and the second reagent disk 30b are disposed inside a first reagent cool box 31a and a second reagent cool box 31b, respectively. In the first reagent cool box 31a and the second reagent cool box 31b, multiple first reagent bottles 32a and second reagent bottles 32b, each attached with a label displaying reagent identification information such as a bar code, are placed along the circumferential direction of the first reagent disk 30a and the second reagent disk 30b, respectively. In each of the first reagent bottles 32a and the second reagent bottles 32b, a reagent liquid corresponding to an analysis item which can be analyzed by the automatic analyzer 1 is stored. Further, to the first reagent cool box 31a and the second reagent cool box 31b, a first bar code reading device 33a, and a second bar code reading device 33b are attached, respectively, and these devices read the bar code displayed on the outer wall of each of the first reagent bottles 32a and the second reagent bottles 32b at the time of registration of the reagent. The read-out reagent information is registered in a memory 56 together with the positions thereof on the first reagent disk 30a and the second reagent disk 30b.

Further, in the vicinities of the first reagent disk 30a and the second reagent disk 30b, a first reagent dispensing mechanism 34a and a third reagent dispensing mechanism 34b, each of which has substantially the same mechanism as that of the sample dispensing mechanism 22 are disposed, respectively. When dispensing the reagent, by a pipette nozzle provided in these mechanisms, the reagent is sucked therein from each of the first reagent bottles 32a and the second reagent bottles 32b corresponding to the test item positioned at reagent receiving positions on the reaction disk 10, and is discharged into the corresponding reaction cell 11.

A first stirring mechanism 35*a* and a second stirring mechanism 35*b* are disposed at positions surrounded by the reaction disk 10, the first reagent disk 30*a*, the second reagent disk 30*b*, the first reagent dispensing mechanism 34*a*, and the third reagent dispensing mechanism 34*b*. The mixed solution of the sample and the reagent stored in the reaction cell 11 is stirred by the first stirring mechanism 35*a* or the second stirring mechanism 35*b* so as to accelerate a reaction.

Here, the light source 40 is disposed near a central portion of the reaction disk 10, the photometer 41 is disposed on an outer circumferential side of the reaction disk 10, and the line of the reaction cells 11 after the stirring is completed is rotationally moved so as to pass through a photometric position sandwiched between the light source 40 and the photometer 41. Incidentally, the light source 40 and the photometer 41 constitute a light detection system. The photometer 41 is a photometer which detects transmitted light or scattered light.

The reaction solution of the sample and the reagent in each reaction cell 11 is subjected to photometry every time the reaction cell passes across the front of the photometer 41 during the rotational motion of the reaction disk 10. An analog signal of scattered light measured for each sample is input to an A/D (analog/digital) converter 54. The inside of the used reaction cell 11 is cleaned by a reaction cell cleaning mechanism 36 disposed in the vicinity of the reaction disk 10, so that the reaction cell can be used repeatedly.

Next, a control system and a signal processing system in the automatic analyzer 1 shown in FIG. 1 will be briefly described. The computer 50 is connected to a sample dispensing control section 52, a reagent dispensing control section 53, and the A/D converter 54 via an interface 51. The computer 50 sends a command to the sample dispensing control section 52 so as to control the sample dispensing operation. Further, the computer 50 sends a command to the reagent dispensing control section 53 so as to control the reagent dispensing operation. A photometric value converted into a digital signal by the A/D converter 54 is put into the computer 50.

A printer 55 for printing, a memory 56 and an external output medium 57, each serving as a memory device, a keyboard 58 for inputting an operation command or the like, and a CRT display (display device) 59 for display on a screen are connected to the interface 51. As the display device 59, a liquid crystal display or the like can be adopted other than the CRT display. The memory 56 is composed of, for example, a hard disk memory or an external memory. The memory 56 stores information such as a password of each operator, a display level of each screen, an analysis parameter, an analysis item request content, a calibration result, and an analysis result.

Next, a sample analysis operation in the automatic analyzer 1 shown in FIG. 1 will be described. The analysis parameter with respect to the item which can be analyzed by the automatic analyzer 1 is previously input via an information input device such as the keyboard 58 and is stored in the memory 56. The operator selects a test item requested for each sample by using an operation function screen.

At this time, information such as a patient ID is also input from the keyboard 58. In order to analyze the test item designated for each sample, the pipette nozzle 24 of the sample dispensing mechanism 22 dispenses a predetermined amount of the sample into the reaction cell 11 from the specimen container 21 in accordance with the analysis parameter.

The reaction cell 11 into which the sample has been dispensed is transported by the rotation of the reaction disk 10 and stops at the reagent receiving position. The pipette nozzles of the first reagent dispensing mechanism 34*a* and the third reagent dispensing mechanism 34*b* dispense a predetermined amount of the reagent liquid into the reaction cell 11 in accordance with the analysis parameter of the corresponding test item. The order of dispensing the sample and the reagent may be opposite to this example, and the reagent may be dispensed prior to the sample.

Thereafter, by the first stirring mechanism 35*a* and the second stirring mechanism 35*b*, the sample and the reagent are stirred and mixed with each other. When the reaction cell 11 passes across the photometric position, the transmitted light or scattered light obtained from the reaction solution is photometrically measured by the photometer 41. The photometrically measured transmitted light or scattered light is converted into a numerical value which is proportional to the light intensity by the A/D converter 54, and the numerical value is put into the computer 50 via the interface 51.

By using this converted numerical value, the concentration data is calculated based on a calibration curve previously measured by an analysis method specified for each test item. The component concentration data as the analysis result of each test item is output to the printer 55 or the screen of the CRT display 59.

Before the above-described measurement operation is executed, the operator performs setting of various parameters and registration of the sample required for the analysis measurement via the operation screen of the CRT display 59. Moreover, the operator confirms the analysis result obtained after the measurement by using the operation screen on the CRT display 59.

FIG. 2 is a schematic view of an automatic analyzer provided with a biochemical analysis section of a turn table system and a coagulation time measurement section according to an embodiment of the invention. The automatic analyzer is configured such that the sample dispensing mechanism 22 is shared by the biochemical analysis section and the coagulation time measurement section, and to the automatic biochemical analyzer of a turn table system shown in FIG. 1, a reaction container supply section 63 in which multiple disposable reaction containers 62 to be used for measurement are stocked, a reaction container temperature control block 60 provided with multiple coagulation time detection sections 61, a reaction container transferring mechanism 65 which transfers the disposable reaction container 62, a second reagent dispensing mechanism with a reagent heating function 66, a coagulation time sample dispensing position 64, and a reaction container discarding section 67 are added. The reaction container temperature control block 60 has a coagulation time detection section 61 and can control the reagent or the reaction solution in the disposable reaction container 62 to have a constant temperature.

In FIG. 3, a coagulation time measurement section cover 68 according to an embodiment of the invention is shown. The coagulation time detection section 61 irradiates light from a light source such as LED onto a mixed liquid of a sample and a reagent, and detects a change in scattered light or transmitted light by the deposition of fibrin, whereby a coagulation time is calculated. Therefore, in order to avoid the effect of ambient light such as indoor lighting or sunlight, the coagulation time measurement section cover 68 for the purpose of shielding light is provided. Further, in the invention, the coagulation time measurement section cover 68 also plays a role in blocking the outside air by covering the second reagent dispensing mechanism with a reagent heating function 66. Inside the coagulation time measurement section cover 68, other than the second reagent dispensing mechanism with a reagent heating function 66, many heat sources such as the reaction container temperature control block 60 and a motor for driving the respective mechanisms are present, and therefore, the temperature inside the coagulation time measurement section cover 68 is inevitably higher than the temperature outside the device. Therefore, when the temperature inside the coagulation time measurement section cover 68 is monitored by a cover's internal temperature sensor 70 disposed inside the coagulation time measurement section cover 68, and heat is exhausted by an exhaust fan 69 which exhausts air inside this cover, the temperature inside the coagulation time measurement section cover 68 can be maintained constant. For example, a predetermined threshold (for example 30° C.) is set for the cover's internal temperature sensor 70, and when the sensor detects a temperature higher than this threshold, the exhaust fan 69 is driven, whereby the temperature can be controlled to be not higher than this threshold.

In FIG. 4, a schematic view of a flow channel of the second reagent dispensing mechanism with a reagent heating function 66 according to an embodiment of the invention is shown. The second reagent dispensing mechanism with a reagent heating function 66 is composed of a reagent probe 71, a reagent heating heat block 72, a reagent dispensing syringe 73, a plunger 74, a solenoid valve 75, and a fluid temperature control mechanism 76, and the inside of the flow channel is filled with an internal fluid (for example, ion exchanged water). By moving the plunger 74 up and down in a state where the solenoid valve 75 is closed, the reagent can be discharged or sucked from the tip end of the reagent probe 71. Further, when the solenoid valve 75 is opened, the pressurized internal fluid flows through the flow channel and flows out from the tip end of the reagent probe 71, whereby the inside of the flow channel can be cleaned.

The fluid temperature control mechanism 76 controls the temperature of the internal fluid of the reagent dispensing syringe 73, and is composed of, for example, a heater which heats the fluid in the flow channel and a control mechanism which controls this heater, and is configured to heat the fluid to a constant temperature and maintains the temperature. According to this configuration, even in the case where the temperature outside the device or the temperature of supply water to the device varies, during the course of discharge of the fluid heated to a constant temperature from the reagent probe 71, the temperature of the flow channel can be maintained substantially constant up to the tip end of the reagent probe 71, and thus, stable reagent heating and dispensing of the reagent with good reproducibility can be realized.

Further, the temperature of air around the flow channel from the reagent probe 71 of the second reagent dispensing mechanism with a reagent heating function 66 to the fluid temperature control mechanism 76 can be controlled to be a constant temperature by the coagulation time measurement section cover 68, the exhaust fan 69, and the cover's internal temperature sensor 70. According to this configuration, more stable reagent heating and higher dispensing accuracy can be realized.

In FIG. 5, one example of a coagulation time measurement sequence according to an embodiment of the invention is shown. The heating of the sample discharged into the disposable reaction container 62 is performed by the coagulation time detection section 61 provided for the reaction container temperature control block 60 of the coagulation time measurement section (b to d), and the reagent is preheated (to 37° C.) in the reaction cell 11 on the reaction disk 10 of the biochemical analysis section (i to j). By this preheating, the temperature of the reagent before sucking is controlled to be a constant temperature. The reagent preheated to 37° C. is further heated (to, for example, 39° C.) by the second reagent dispensing mechanism with a reagent heating function 66, and discharged into the disposable reaction container 62 containing the sample having already been heated to 37° C., and a blood coagulation reaction is started (e). After the reaction is completed (f), a coagulation time is calculated (g), and the disposable reaction container 62 is discarded to the reaction container discarding section 67 (h). Further, in the reaction cell 11 after the preheated reagent is sucked, cleaning water or a cleansing agent is discharged by the third reagent dispensing mechanism 34*b* (k), and thereafter, the reaction cell is cleaned by the reaction cell cleaning mechanism 36 (l).

The measurement of a coagulation time shown in FIG. 5 is performed as follows. The temperature inside the coagulation time measurement section cover 68 is maintained to be constant at a temperature lower than 37° C. (for example, 30° C.), and the reagent preheated to 37° C. in the reaction cell 11 is drawn in the reagent heating heat block 72 from the reagent probe 71, heated to a temperature higher than 37° C. (for example, 39° C.), and discharged into the disposable reaction container 62 whose temperature is controlled to be 37° C. together with the sample by the reaction container temperature control block 60, and a coagulation time is measured in a state where the internal fluid is controlled to have a temperature lower than that of the reagent heating heat block 72 (for example, 30° C.) by the fluid temperature control mechanism 76. In this manner, by controlling the temperature such that the control temperature of the fluid temperature control mechanism 76 is lower than the control temperature of the second reagent dispensing mechanism with a reagent heating function 66, stable reagent heating and dispensing of the reagent with high accuracy can be achieved independent of the temperature outside the device and the temperature of supply water to the device.

In FIG. 6, one example of a state of controlling the temperature around the reagent dispensing mechanism with a heating function according to an embodiment of the invention is shown. It is desired to control the temperature inside the coagulation time measurement section cover 68 and the temperature of the internal fluid to be the same temperature for the purpose of maintaining the temperature of the internal fluid which has a great influence on the dispensing accuracy of the dispensing of the reagent to be constant. In the case of performing control to be the same temperature, it is desired to configure the device such that the temperature inside the coagulation time measurement section cover and the temperature of the internal fluid can be controlled by one temperature setting as the setting of the device. In this embodiment, the temperature inside the coagulation time measurement section cover 68 and the temperature of the internal fluid are both controlled to be 30° C. Incidentally, the term "same" as used herein accepts a difference by up to about ±2° C. as an error.

It is desired that the preheating temperature of the reagent and the temperature of the reagent heating heat block 72 are as close as possible to each other and also the preheating temperature of the reagent is not higher than the temperature of the reagent heating heat block. In this embodiment, the preheating temperature of the reagent is controlled to be 37° C., and the temperature of the reagent heating heat block is controlled to be 39° C.

In FIGS. 7(a) to 7(d), the flow of the dispensing operation in the case where segmental air is sucked inside the coagulation time measurement section cover 68 according to an embodiment of the invention is shown. The segmental air is required for preventing the reagent from being thinned with the internal fluid, but has a great influence on the dispensing accuracy, reproducibility, and the like because the volume thereof is changed by a change in temperature, and therefore, it is very important to control the temperature of the segmental air when sucking and to control the amount of change in the temperature of the segmental air after sucking. In this embodiment, the change in the temperature of the segmental air is controlled to be from 30° C. to 39° C.

In FIGS. 8(a) to 8(d), the flow of the dispensing operation in the case where the segmental air is sucked inside the reaction cell according to an embodiment of the invention is shown. The importance of the control of the temperature of the segmental air when sucking and the control of the amount of change in the temperature of the segmental air after sucking is as described above, however, by decreasing the amount of change in the temperature of the segmental air is as much as possible, the change in the volume of the segmental air can be decreased, and thus, it becomes possible to improve the dispensing accuracy. In this embodiment, by sucking the segmental air inside the reaction cell, that is, at a position which is lower than the opening surface of the reaction cell, the change in the temperature of the segmental air is decreased (from 37° C. to 39° C.) as compared with the change from 30° C. to 39° C. as shown in FIG. 7. Due to this, it can be expected to further improve the dispensing accuracy. Further, although the temperature inside the coagulation time measurement section cover 68 results in being controlled within the range of 30° C.±several degrees, the temperature of the thermostat bath 12 to be used for controlling the temperature of the reaction cell 11 is controlled to be 37±0.1° C., and therefore, it is possible to more stably control the temperature of the segmental air.

FIG. 9 is a view showing the second reagent dispensing mechanism with a heating function 66 provided with a block which makes the temperature around the reagent dispensing probe constant when discharging the reagent according to an embodiment of the invention. When the reagent is discharged into the disposable reaction container 62, by discharging the reagent in a state where the reagent dispensing probe is inserted into a heat block 77 for use prior to dispensing, which has a through-hole capable of inserting the reagent dispensing probe therethrough, and is controlled to have a constant temperature (for example, 37±0.3° C.), it becomes possible to more accurately control the temperature as compared with the case where only the temperature inside the coagulation time measurement section cover 68 is controlled. Further, even in the case where the temperature inside the coagulation time measurement section cover 68 is not controlled, a reagent dispensing system which is less susceptible to the effect of the temperature outside the device can be constructed. Incidentally, this heat block 77 for use prior to dispensing is provided at a position different from the reagent sucking position, and therefore, the reagent is sucked without inserting the reagent dispensing probe into the heat block 77 for use prior to dispensing. This heat block 77 for use prior to dispensing may be provided also at the reagent sucking position, however, it is possible to decrease the number of components of the heat block 77 for use prior to dispensing as compared with the case where the heat block 77 is not provided.

FIG. 10 additionally shows an installation example of the heat block 77 for use prior to dispensing. The heat block 77 for use prior to dispensing is disposed at a midpoint between the reagent sucking position and the coagulation time detection section 61. It takes several seconds (for example 3 to 4 seconds) to heat the reagent by the second reagent dispensing mechanism with a reagent heating function 66 after sucking the reagent, and therefore, by heating the reagent in a state where the reagent dispensing probe is inserted into the heat block 77 for use prior to dispensing, the variation in the temperature of the reagent dispensing probe can be suppressed. Further, by discharging the reagent while inserting the reagent dispensing probe into the disposable reaction container 62 whose temperature is controlled to be 37° C. by the reaction container temperature control block 60, the temperature of the reagent when discharging the reagent can be stabilized.

Further, a configuration in which the reaction container temperature control block 60 and the heat block 77 for use prior to dispensing are commonized, the reagent dispensing probe is moved to the coagulation time detection section 61 promptly after sucking the reagent, and the heating and discharge of the reagent are performed in a state where the reagent dispensing probe is inserted into the disposable reaction container 62 whose temperature is controlled to be 37° C. can also be adopted.

According to the configuration as the embodiment, it is possible to provide an automatic analyzer capable of performing an analysis with high reproducibility regardless of a variation in the temperature outside the device and the temperature of supply water to the device.

REFERENCE SIGNS LIST

1: automatic analyzer
10: reaction disk
11: reaction cell
12: thermostat bath
13: thermostat device
20: sample disk
21: specimen container
22: sample dispensing mechanism
23: movable arm
24: pipette nozzle
30a: first reagent disk
30b: second reagent disk
31a: first reagent cool box
31b: second reagent cool box
32a: first reagent bottle
32b: second reagent bottle
33a: first bar code reading device
33b: second bar code reading device
34a: first reagent dispensing mechanism
34b: third reagent dispensing mechanism
35a: first stirring mechanism
35b: second stirring mechanism
36: reaction cell cleaning mechanism
40: light source
41: photometer
50: computer
51: interface
52: sample dispensing control section
53: reagent dispensing control section
54: A/D converter 55: printer
56: memory
57: external output medium
58: keyboard
59: CRT display (display device)
60: reaction container temperature control block
61: coagulation time detection section
62: disposable reaction container
63: reaction container supply section
64: coagulation time sample dispensing position
65: reaction container transferring mechanism
66: second reagent dispensing mechanism with reagent heating function
67: reaction container discarding section
68: coagulation time measurement section cover
69: exhaust fan
70: cover's internal temperature sensor
71: reagent probe
72: reagent heating heat block
73: reagent dispensing syringe
74: plunger
75: solenoid valve
76: fluid temperature control mechanism
77: heat block for use prior to dispensing

The invention claimed is:

1. An automatic analyzer comprising:
a reaction disk, on which reaction cells are arranged on the circumference thereof, and which alternately repeats rotating and stopping;
a sample dispensing mechanism which dispenses a sample into the reaction cells and into a disposable reaction container at a predetermined position;
a first reagent dispensing mechanism which dispenses a reagent into the reaction cells;
a thermostat bath disposed around the reaction disk that is configured to heat the reagent or a reaction solution in the reaction cells to have a first constant temperature;
a light source to irradiate light towards the reaction disk;
a photometer which detects transmitted light or scattered light by irradiating the light onto the reaction solution in one of the reaction cells on the reaction disk from the light source;
a reaction container temperature control block which has a coagulation time detection section;
a reaction container transferring mechanism that transfers the disposable reaction container from the predetermined position to the coagulation time detection section;
a second reagent dispensing mechanism which dispenses the reagent from one of the reaction cells into the disposable reaction container at the coagulation time detection section; and
a controller configured to control the reaction disk, the sample dispensing mechanism, the first reagent dispensing mechanism, the thermostat bath, the light source, the photometer, and the reaction container temperature control block,
wherein the coagulation time detection section respectively includes a light source and a photometer which detects transmitted light or scattered light by irradiating light onto a reaction solution in the disposable reaction container arranged thereon, and the reaction container temperature control block is a heat source configured to heat the reaction solution in the disposable reaction container to have a second constant temperature,
wherein the second reagent dispensing mechanism includes a reagent probe, a reagent heating block configured to heat the reagent in the reagent probe to have a third constant temperature, a reagent dispensing syringe which is connected to the reagent probe through the reagent heating block, and a fluid temperature control mechanism which is disposed upstream of the reagent dispensing syringe and configured to heat an internal fluid of the reagent dispensing syringe to have a fourth constant temperature,
wherein the reagent heating block is disposed on a flow channel of the second reagent dispensing mechanism between the reagent dispensing syringe and the reagent probe,
wherein the controller is configured to control the thermostat bath to heat the reagent or the reaction solution in the reaction cells to have the first constant temperature, the reaction container temperature control block to heat the reaction solution in the disposable reaction container to have the second constant temperature, the reagent heating block to heat the reagent in the reagent probe to have the third constant temperature, and the fluid temperature control mechanism to heat the internal fluid to have the fourth constant temperature, and
wherein the third constant temperature is different from the fourth constant temperature.

2. The automatic analyzer according to claim 1, wherein the fourth constant temperature of the fluid temperature control mechanism is lower than the third constant temperature of the reagent heating block.

3. The automatic analyzer according to claim 1, further comprising:
a cover which covers the second reagent dispensing mechanism;
a temperature sensor disposed inside the cover; and
a fan which exhausts air inside the cover,
wherein, when the temperature sensor detects a temperature higher than a predetermined threshold, the fan is driven.

4. The automatic analyzer according to claim 3, wherein the temperature inside the cover and the fourth constant temperature of the internal fluid are controlled to be a same temperature.

5. The automatic analyzer according to claim 1, wherein when the second reagent dispensing mechanism sucks the reagent from one of the reaction cells of the reaction disk, air in the one of the reaction cells is sucked into the reagent probe which separates the reagent and the internal fluid from each other in the reagent probe.

6. The automatic analyzer according to claim 5, wherein the reagent in the one of the reaction cells is heated by the thermostat bath to the first constant temperature which is greater than the fourth constant temperature of the internal fluid.

7. The automatic analyzer according to claim 1, further comprising:
a heat block located at a position different from the reaction disk, which has a through-hole in which the reagent probe of the second reagent dispensing mechanism is inserted, and which is controlled to have the first constant temperature, and
wherein the reagent is discharged into the disposable reaction container in a state where the reagent probe is inserted into the through-hole.

8. The automatic analyzer according to claim 7, wherein the reagent is sucked without inserting the reagent dispensing probe into the heat block.

9. The automatic analyzer according to claim 1, further comprising:

a heat block located at a position different from the reaction disk, which has a through-hole in which the reagent probe of the second reagent dispensing mechanism is inserted, and which is controlled to have the first constant temperature, and the reagent in the second reagent dispensing mechanism is heated by the heat block in a state where the reagent probe is inserted into the through-hole.

10. The automatic analyzer according to claim 9, wherein the reagent is discharged in a state where the reagent probe is inserted into the disposable reaction container disposed in the coagulation time detection section.

11. The automatic analyzer according to claim 1, wherein the heating of the reagent and the discharge of the reagent are performed by the second reagent dispensing mechanism in a state where the reagent probe is inserted into the disposable reaction container disposed in the coagulation time detection section.

12. The automatic analyzer according to claim 1, further comprising:

a reaction container supply section which holds a plurality of the disposable reaction containers adjacent to the coagulation time detection section.

13. The automatic analyzer according to claim 1, wherein the first constant temperature is equal to the second constant temperature, the third constant temperature is greater than the first constant temperature, and the fourth constant temperature is less than the first constant temperature.

14. The automatic analyzer according to claim 1, wherein the first constant temperature is 37° C., the second constant temperature is 37° C., the third constant temperature is greater than 37° C., and the fourth constant temperature is less than 37° C.

15. The automatic analyzer according to claim 14, wherein the third constant temperature is 39° C., and the fourth constant temperature is 30° C.

* * * * *